United States Patent
Tseng (12) 
(10) Patent No.: US 10,598,618 B2
(45) Date of Patent: Mar. 24, 2020

(54) DETACHABLE BOILING POINT DETECTOR FOR BRAKE FLUID

(71) Applicant: CHUAN JIING ENTERPRISE CO., LTD., Taichung (TW)

(72) Inventor: Tien Tsai Tseng, Taichung (TW)

(73) Assignee: CHUAN JIING ENTERPRISE CO., LTD., Taichung (TW)

( * ) Notice: Subject to any disclaimer, the term of this patent is extended or adjusted under 35 U.S.C. 154(b) by 236 days.

(21) Appl. No.: 15/794,936

(22) Filed: Oct. 26, 2017

(65) Prior Publication Data

US 2019/0128826 A1    May 2, 2019

(51) Int. Cl.
| | |
|---|---|
| *G01N 25/08* | (2006.01) |
| *B60T 17/22* | (2006.01) |
| *F16D 66/00* | (2006.01) |
| *B61H 1/00* | (2006.01) |

(52) U.S. Cl.
CPC .......... *G01N 25/08* (2013.01); *B60T 17/221* (2013.01); *B61H 1/00* (2013.01); *F16D 2066/001* (2013.01)

(58) Field of Classification Search
CPC .................................................. G01N 25/08
USPC ........................................................ 374/27
See application file for complete search history.

(56) References Cited

U.S. PATENT DOCUMENTS

| | | | | |
|---|---|---|---|---|
| 5,380,091 | A | * | 1/1995 | Buchanan ............... G01N 25/08 374/16 |
| 5,785,425 | A | * | 7/1998 | Buchanan ............... G01N 25/08 374/16 |
| 5,814,721 | A | * | 9/1998 | Mills .................. G01N 33/2847 374/16 |
| 2012/0216605 | A1 | * | 8/2012 | Silveri ................... G01N 27/08 73/61.41 |
| 2013/0016755 | A1 | * | 1/2013 | Tseng ..................... G01N 25/08 374/16 |
| 2016/0381822 | A1 | * | 12/2016 | Hausler ................ H05K 5/0065 361/752 |

* cited by examiner

*Primary Examiner* — Clayton E. LaBalle
*Assistant Examiner* — Leon W Rhodes, Jr.
(74) *Attorney, Agent, or Firm* — Muncy, Geissler, Olds & Lowe, PC (57) ABSTRACT

A detachable boiling point detector for brake fluid includes a holding portion and a detecting portion connected to the holding portion. The holding portion has a connecting portion, and an assembling end of the detecting portion is detachably connected to the connecting portion. The detecting portion has a heater and a temperature sensor which are connected to a first port. A first circuit board and a second circuit board are assembled in the holding portion and spaced by a distance. A second port is assembled on the second circuit board and facing the detecting portion. The first port is detachably combined with the second port. When the detecting portion is connected to the holding portion, the first port and the second port are combined with each other at a connection between the assembling end and the connecting portion.

7 Claims, 9 Drawing Sheets

FIG. 9
PRIOR ART

DETACHABLE BOILING POINT DETECTOR FOR BRAKE FLUID

BACKGROUND OF THE INVENTION

Field of the Invention

The present invention relates to the structure of a boiling point detector for brake fluid, in particular to a detachable boiling point detector for brake fluid.

Description of the Prior Art

Figure 8:
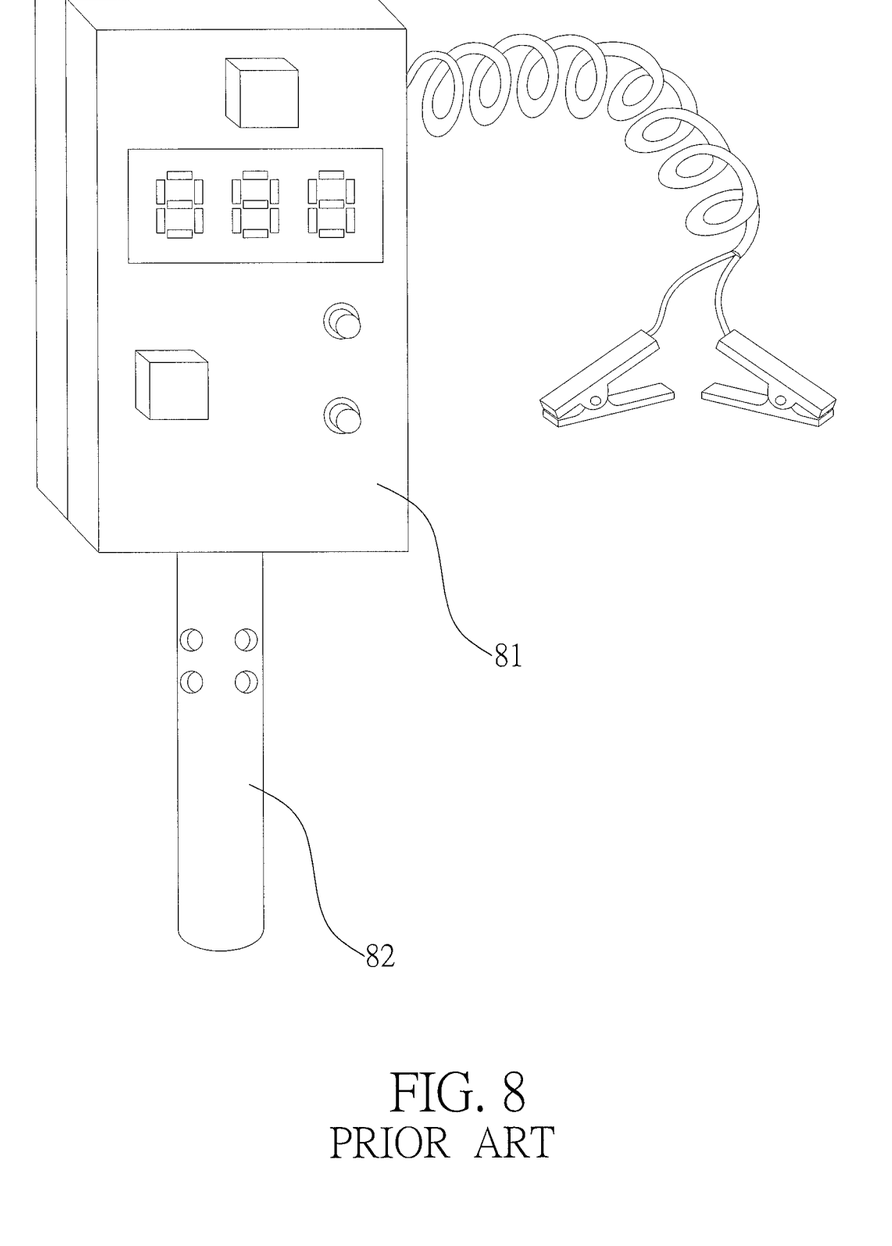
FIG. 8 illustrates a structural view of a conventional boiling point detector for brake fluid.

As shown in FIG. 8, a conventional boiling point detector for brake fluid includes a testing machine 81 and a testing bar 82. A heater and a thermometer are assembled in the testing bar 82. In operation, the testing bar 82 is immersed into a brake fluid A and the brake fluid is heated A to be boiling by the heater. Hence, the thermometer measures the boiling point of the brake fluid A to check if the brake oil A turns deteriorated.

However, in the conventional, the testing bar 82 and the testing machine 81 are firmly connected with each other and cannot be separated from each other, and the testing bar 82 has to be contact with the brake fluid in high temperature frequently and may be broken easily. As a result, repairing the conventional detector is neither easy nor convenient.

Moreover, in the conventional, the detection may be interfered by the noises of the electronic components within the testing machine 81 during the operation, the heat, or the environment temperature, and the accuracy of the detector may be insufficient.

Figure 9:
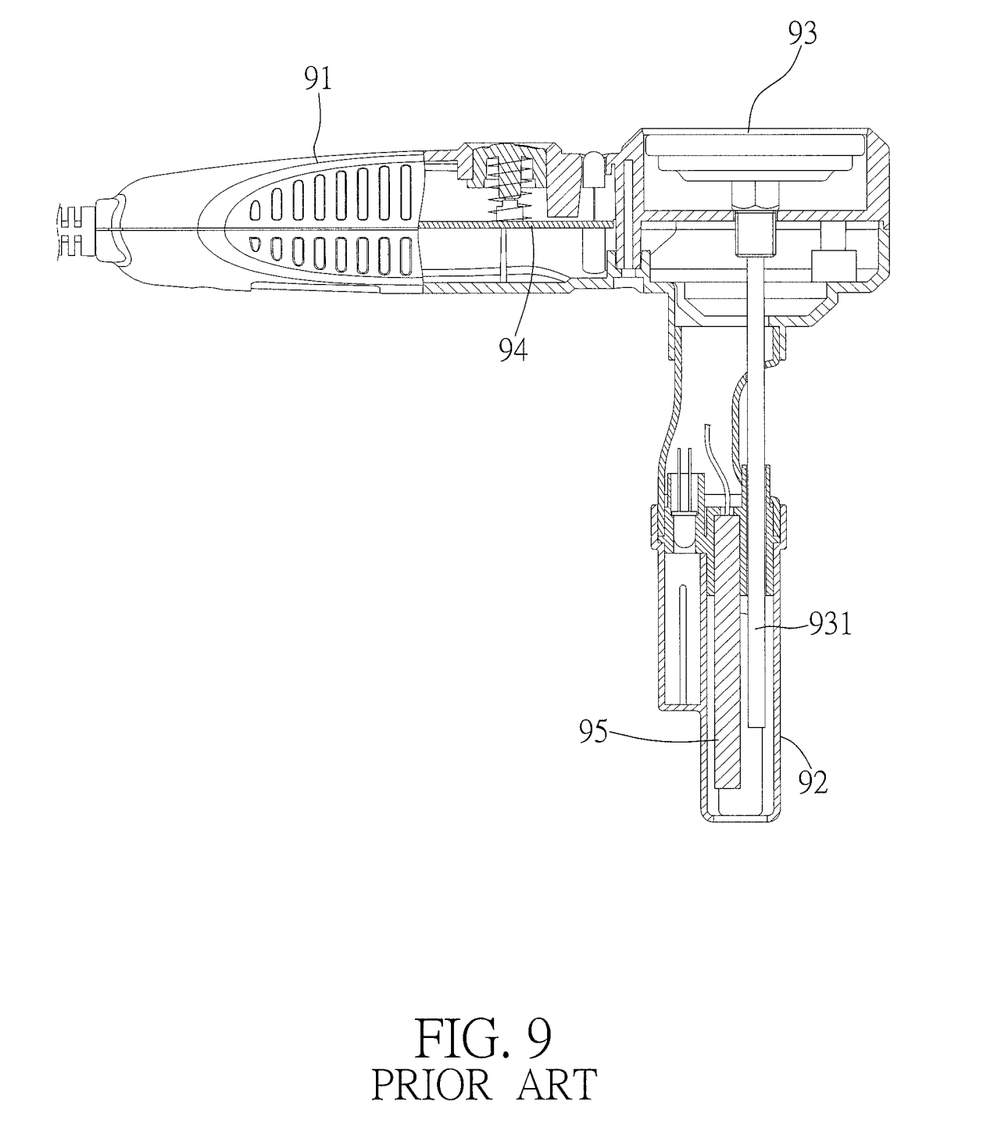
FIG. 9 illustrates a structural view of another conventional boiling point detector for brake fluid.

As shown in FIG. 9, another conventional boiling point detector for brake fluid is illustrated. The detector has a handle 91 and a detecting bar 92 vertically connected to the handle 91. A mechanical thermometer 93 is assembled on the handle 91, and the thermometer 93 has a probe 931 extending toward the interior of the detecting bar 92. A heater 95 is assembled in the detecting bar 92 and connected to a motherboard 94.

Since the probe 931 cannot be detached from the thermometer 93 and the heater 95 cannot be detached from the motherboard 94, the detecting bar 92 cannot be detached from the handle 91 easily, and the package of the product would have a moderate volume. Furthermore, the detecting bar 92 cannot be disassembled easily for replacing the heater 95.

Moreover, even though the mechanical thermometer 93 has less noise interferences, the accuracy of the measurement of the mechanical thermometer is apparently worse than that of the electronic thermometer.

Therefore, how to solve the problem is an issue.

SUMMARY OF THE INVENTION

One object of the present invention is to provide a detachable boiling point detector for brake fluid which is easy to be disassembled. Therefore, the volume of the package of the detector can be reduced and repairing the detector is easy and convenient.

Another object of the present invention is to provide a detachable boiling point detector for brake fluid. The detector is prone to be interfered by neither the noises and the heat generated by the electronic components in the detector during the operation nor the ambient temperature. Therefore, the detection accuracy of the detector is improved.

Yet another object of the present invention is to provide a detachable boiling point detector for brake fluid. Wherein, the vapor of the brake fluid generated by heating the brake fluid to the boiling point would not apply adversely influences to the electronic components in the holding portion.

In view of these, a detachable boiling point detector for brake fluid is provided and the detector comprises a holding portion and a detecting portion connected to the holding portion. A receiving space is formed in the holding portion. A first circuit board is assembled in the receiving space. The first circuit board has a switch being controllable out of the holding portion. A heater is assembled to the detecting portion. Wherein, one side of the holding portion has a connecting portion. The detecting portion has an assembling end and a detecting end opposite to the assembling end. The assembling end is detachably connected to the connecting portion. The heater and a first temperature sensor is assembled on the detecting end. The heater and the first temperature sensor are connected to a first port located at the assembling end via a wire, respectively. A second circuit board is assembled in the receiving space of the holding portion and adjacent to the connecting portion. The second circuit board is electrically connected to the first circuit board. A distance is between the second circuit board and the first circuit board. The second circuit board has a first side surface facing the connecting portion, and a second port is assembled on the first side surface of the second circuit board. The first port is detachably combined with the second port. Wherein, when the detecting portion is connected to the holding portion, the first port and the second port are combined with each other at a connection between the assembling end and the connecting portion.

In one embodiment, two ends of the connecting portion are hollowed. The holding portion has a head portion, and one side of the head portion has a protruding portion adjacent to the connecting portion. A chamber is formed in the protruding portion and in communication with the receiving space and the connecting portion. The second circuit board is assembled in the chamber to block the receiving space from communicating with the connecting portion.

Furthermore, the assembling end of the detecting portion is detachably fitted over the connecting portion and fastened by a locking member.

In one embodiment, the second circuit board has a second side surface distant from the connecting portion. A second temperature sensor, a temperature compensation component, and a temperature signal amplifier are assembled on the second side surface of the second circuit board. Wherein, when a temperature detected by the first temperature sensor is transmitted to the second circuit board, the second temperature sensor on the second circuit board detects a temperature on the second circuit board. The temperature compensation component performs a temperature compensation process to obtain a compensated temperature according to a difference between the temperature detected by the first temperature sensor and the temperature detected by the second temperature sensor. The temperature signal amplifier amplifies a temperature signal of the compensated temperature and transmits the amplified signal to the first circuit board, and a detection result is displayed on a display.

In one embodiment, the detecting portion comprises a sleeve member, a plug, and a cover. Two ends of the sleeve member are hollowed and tubular shaped. One end of the sleeve member forms the assembling end. The plug has a first extending portion and a second extending portion extending opposite to the first extending portion. An engaging block is protruding from the first extending portion. The first extending portion of the plug is assembled in the sleeve member. The engaging block of the plug is engaged with an engaging groove of the sleeve member. A copper pipe is fitted over the second extending portion of the plug. The copper pipe has an opening, and a first heating space is formed in the copper pipe. The cover is hollowed and is fitted over the sleeve member to cover the plug and the copper pipe to form the detecting end.

Furthermore, a second heating space is formed between the cover and the copper pipe. A notch is recessed form the second extending portion of the plug and in communication with the first heating space and the second heating space.

Furthermore, two conductive tubes are passing through the plug. The two conductive tubes are spaced from and aligned parallel with each other. One of two ends of each of the two conductive tubes is extending out of the first extending portion to form a first end toward the sleeve member, and the other end of each of the two conductive tubes is extending out of the second extending portion to form a second end distant from the sleeve member. The first ends of the two conductive tubes are connected to the first port at the assembling end via the wire of the heater. Two inserting ends of the heater are respectively inserted into and fastened with the second ends of the two conductive tubes.

The purposes and the advantages of the present invention can be understood from the embodiments and the drawings.

DETAIL DESCRIPTION OF THE PREFERRED EMBODIMENTS

Figure 1:
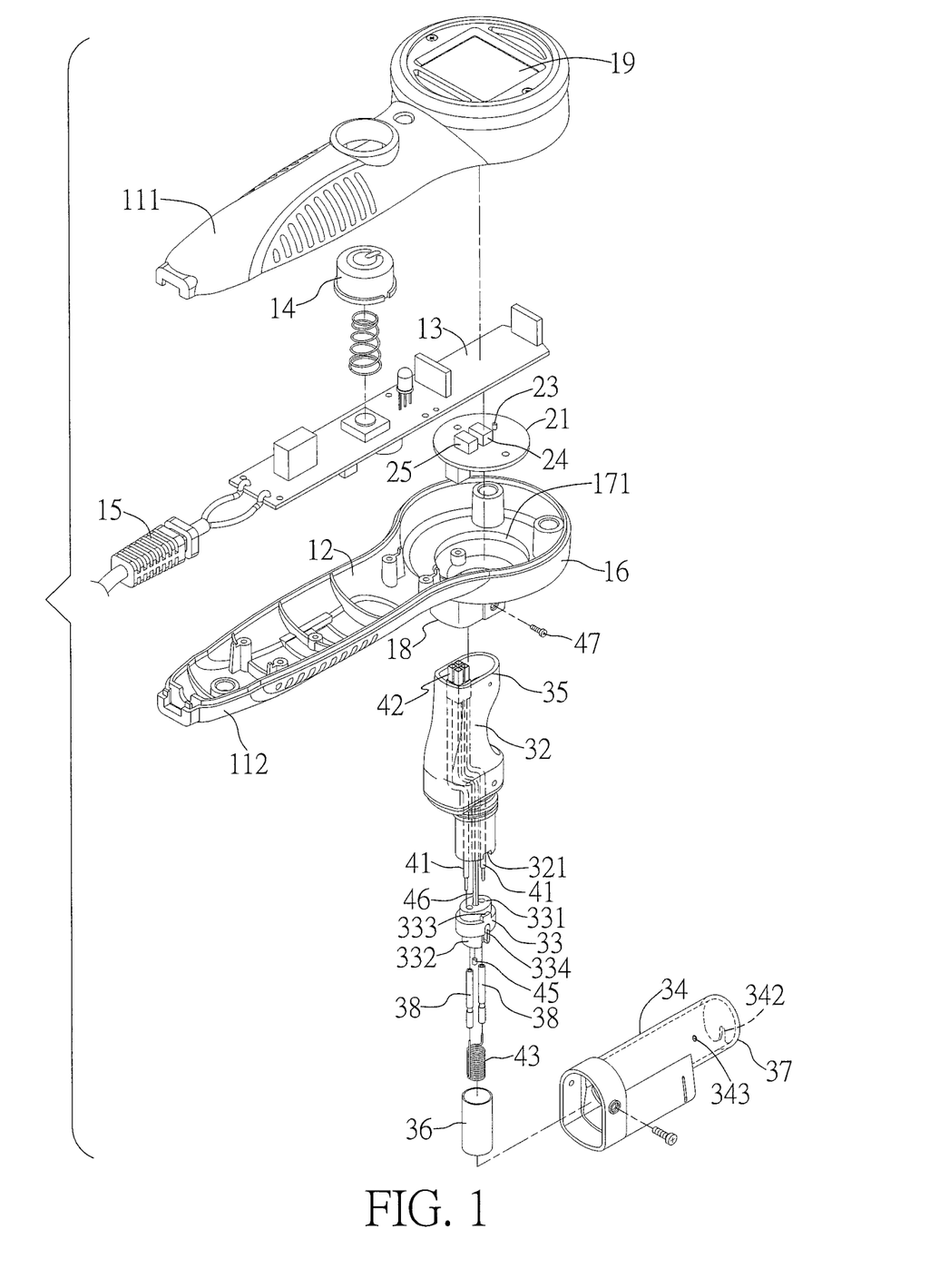
FIG. 1 illustrates an exploded view of a detachable boiling point detector for brake fluid according to an exemplary embodiment of the present invention.
Figure 2:
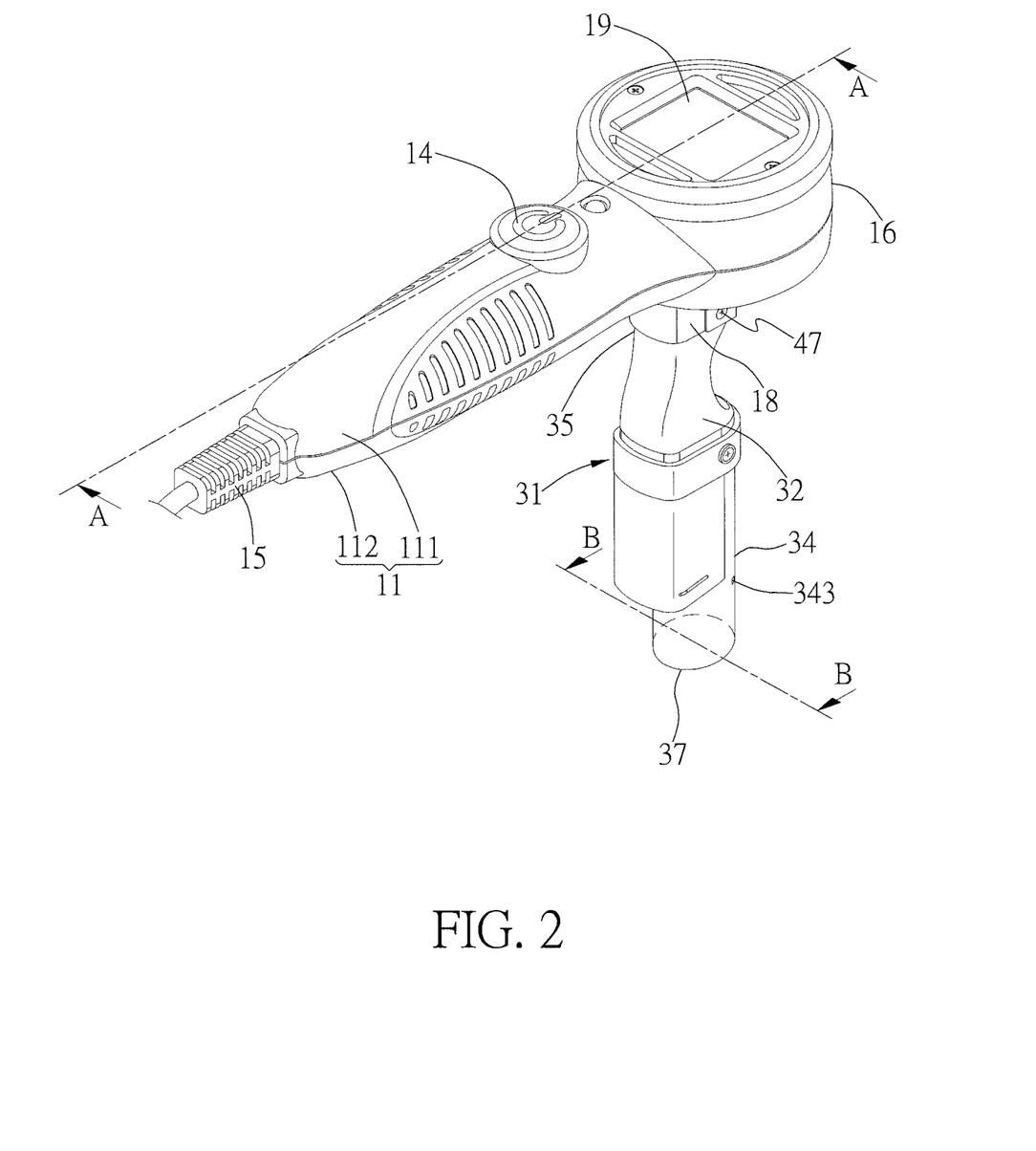
FIG. 2 illustrates a perspective view of the detachable boiling point detector for brake fluid.
Figure 3:
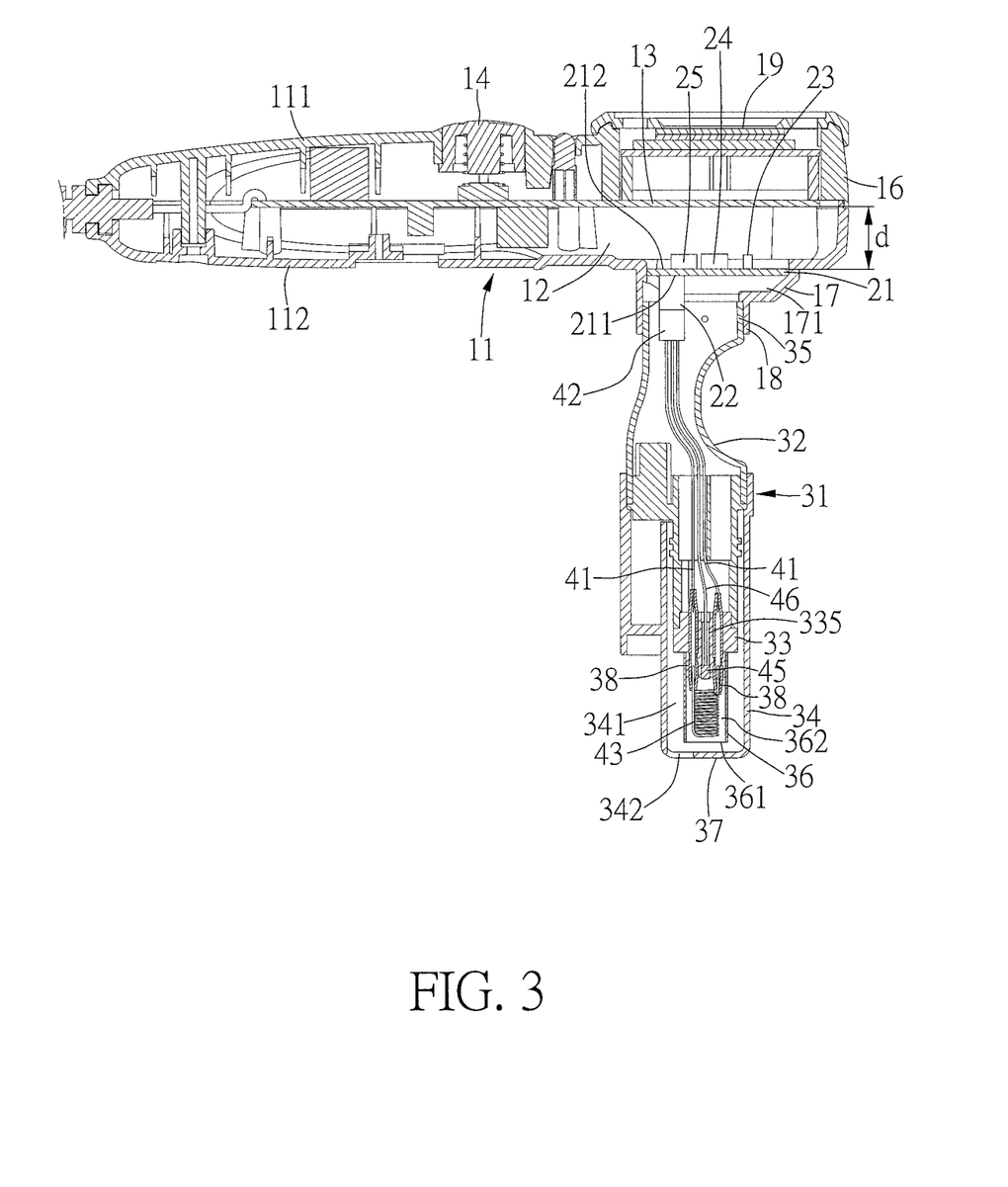
FIG. 3 illustrates a cross-sectional view along line A-A shown in FIG. 2.

Please refer to FIGS. 1 to 3. In this embodiment, the detector comprises a holding portion 11 and a detecting portion 31 vertically connected to the holding portion 11. The holding portion 11 is formed by combining a first housing 111 with a second housing 112, so that a receiving space 12 is formed in the holding portion 11. A first circuit board 13 is assembled in the receiving space 12. The first circuit board 13 has a switch 14, and the user can control the switch 14 out of the first housing 111 of the holding portion 11. The first circuit board 13 is electrically connected to a power wire 15. The holding portion 11 has a head portion 16. One of two sides of the head portion 16 has a protruding portion 17 and a connecting portion 18 adjacent to the protruding portion 17, and two ends of the connecting portion 18 are hollowed. The other side of the head portion 16 has a display 19. A chamber 171 is formed in the protruding portion 17 and in communication with the receiving space 12 and the connecting portion 18. A second circuit board 21 is assembled in the chamber 171 and electrically connected to the first circuit board 13. A distance d is between the first circuit board 13 and the second circuit board 21. The profile of the second circuit board 21 matches with the shape of the chamber 171 to block the receiving space 12 from communicating with the connecting portion 18. One of two side surfaces of the second circuit board 21 faces the connecting portion 18, and the side surface 211 of the second circuit board 21 has a second port 22. A second temperature sensor 23, a temperature compensation component 24, and a temperature signal amplifier 25 are assembled on the other side surface 212 of the second circuit board 21.

The detecting portion 31 comprises a sleeve member 32, a plug 33, and a cover 34. Two ends of the sleeve member 32 are hollowed and tubular shaped. The sleeve member 32 has an assembling end 331 detachably fitted over the connecting portion 18 and fastened by a locking member 47. The plug 33 has a first extending portion 331 and a second extending portion 332 extending opposite to the first extending portion 331. An engaging block 333 is protruding from the first extending portion 331. The first extending portion 331 of the plug 33 is assembled in the sleeve member 32. The engaging block 333 of the plug 33 is engaged with an engaging groove 321 of the sleeve member 32. A copper pipe 36 is fitted over the second extending portion 332 of the plug 33. The copper pipe 36 has an opening 361 and a first heating space 362 is formed in the copper pipe 36. The cover 34 is hollowed and is fitted over the sleeve member 32 to cover the plug 33 and the copper pipe 36 to form a detecting end 37 extending opposite from the assembling end 35.

Figure 4:
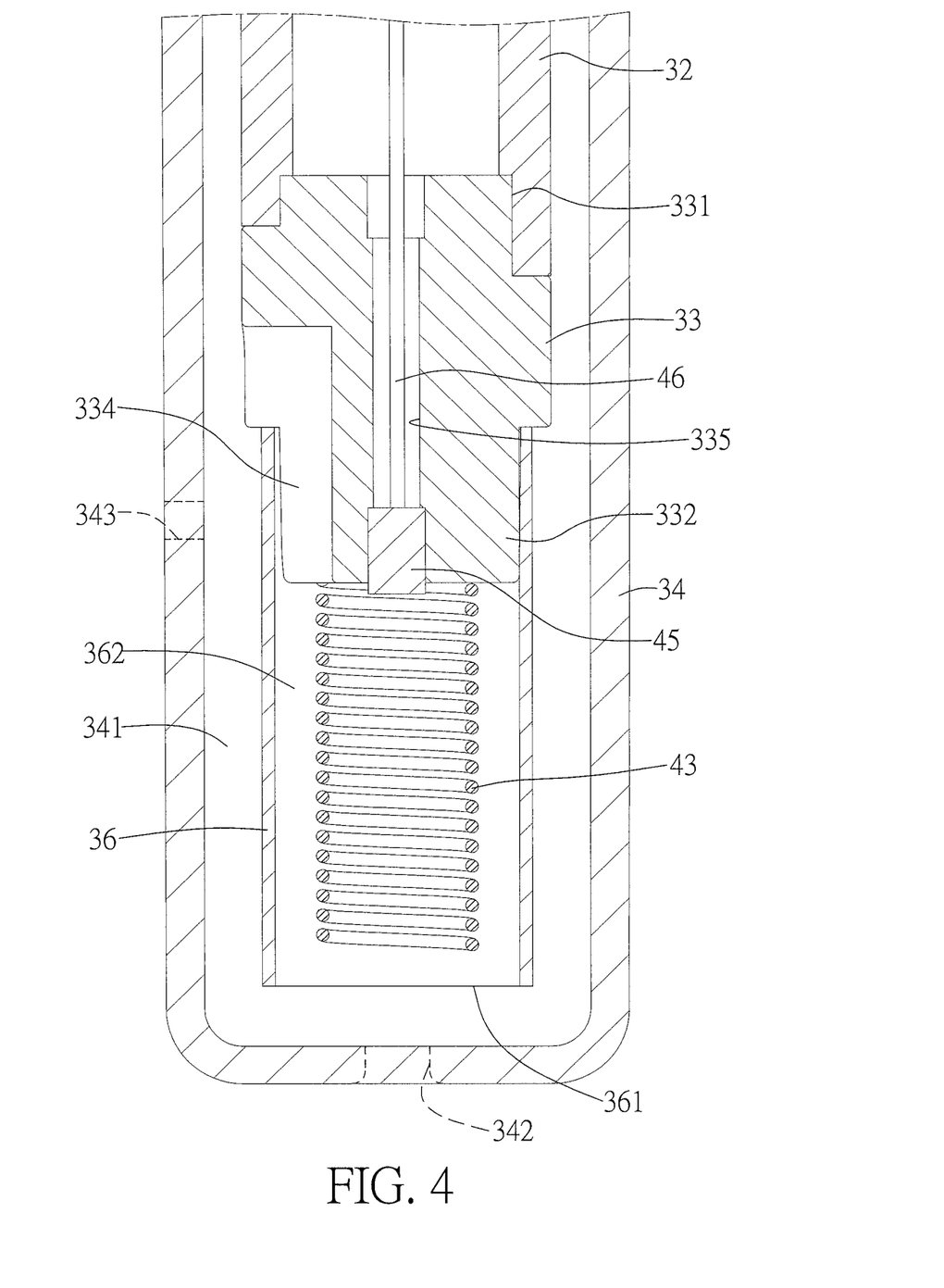
FIG. 4 illustrates a cross-sectional view along line B-B shown in FIG. 2.

Please refer to FIG. 4. A second heating space 341 is formed between the cover 34 and the copper pipe 36. The cover 34 has a first through hole 342 and a second through hole 343. The first through hole 342 and the second through hole 343 are respectively in communication with the second heating space 341. The first through hole 342 is located at one end of the cover 34 and distant from the sleeve member 32, and the second through hole 343 is located on a portion of the cover 34 and adjacent to the plug 33. A notch 334 is recessed from the second extending portion 332 of the plug 33 and in communication with the first heating space 362 and the second heating space 341 for allowing the reflow of the vapor of the brake fluid.

Figure 5:
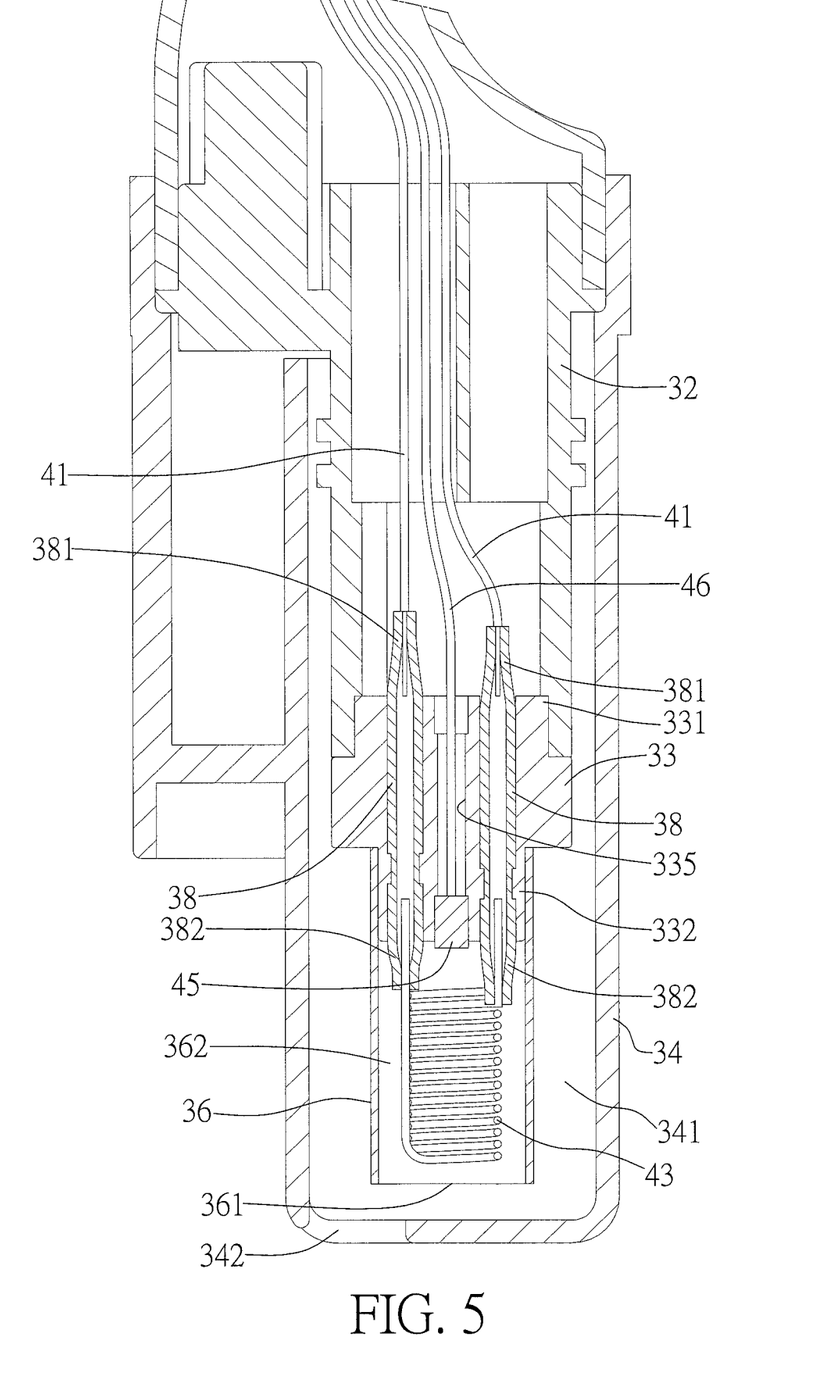
FIG. 5 illustrates an enlarged cross-sectional view along line B-B shown in FIG. 2.

Please refer to FIG. 5. Two conductive tubes 38 are passing through the plug 33 and the two conductive tubes 38 are spaced from and aligned parallel with each other. Two ends of each of the two conductive tubes 38 are respectively extending out of the first extending portion 331 and the second extending portion 332 to form a first end 381 toward the sleeve member 32 and a second end 382 distant from the sleeve member 32. The first ends 381 of the two conductive tubes 38 are connected to a first port 42 at the assembling end 35 via wires 41. The first port 42 is provided for connecting to a second port 22 of the second circuit board 21. The second ends 382 of the two conductive tubes 38 are connected to a heater 43. In this embodiment, the first port 42 and the second port 22 are respectively the conventional plug connector and receptacle connector. In this embodiment, the heater 43 has two inserting ends 44 respectively inserted into and fastened with the second ends 382 of the two conductive tubes 38. The wires 41 are inserted into the first ends 381 of the two conductive tubes 38. Therefore, the heater 43 can be assembled with the detector quickly. The plug 33 has a through hole 335, and the through hole 335 is defined through an axial direction of the plug 33. A first temperature sensor 45 is assembled in the through hole 335 and in communication with the first heating space 362, and the first temperature sensor 45 is connected to the first port 42 via a wire 46.

Figure 6:
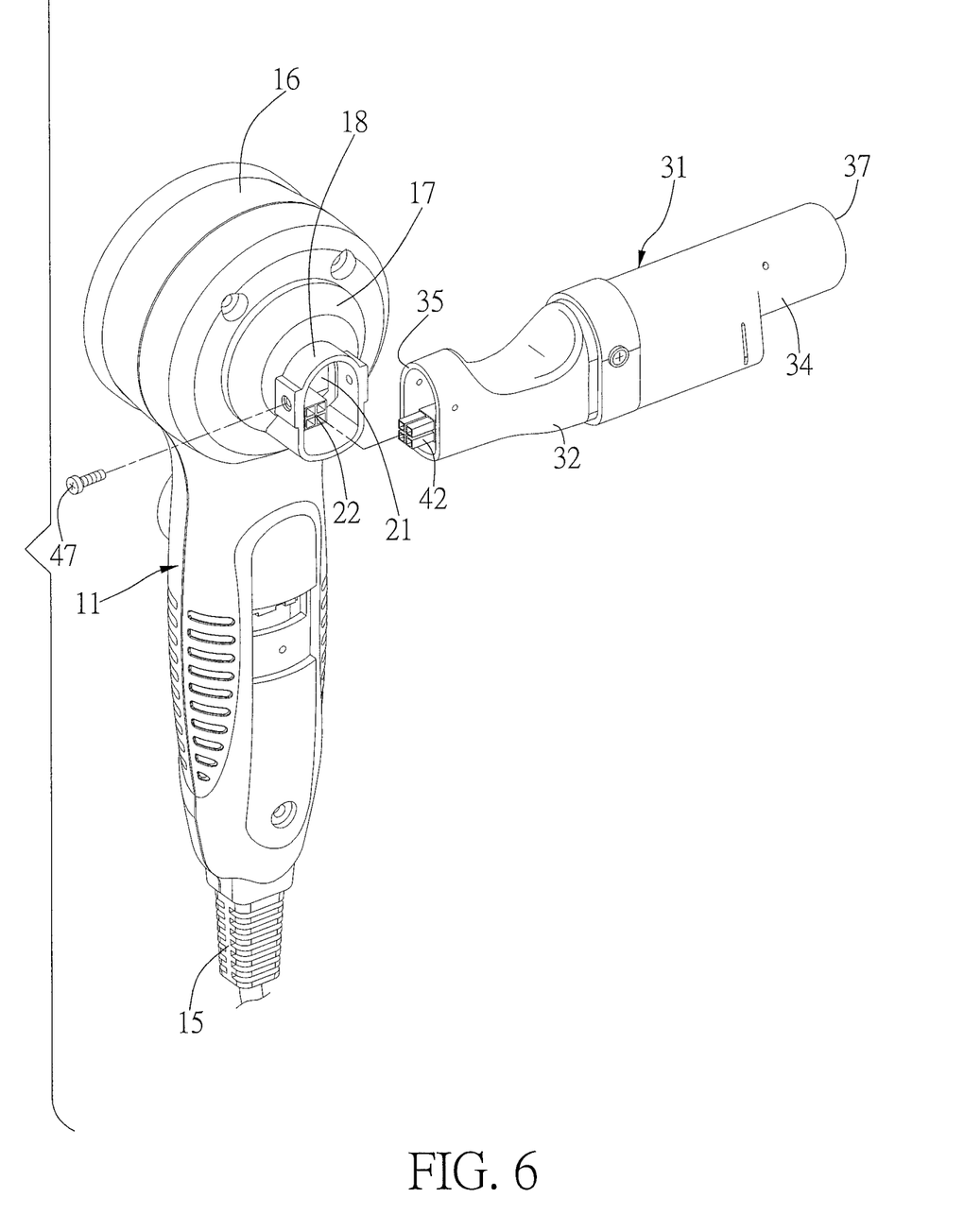
FIG. 6 illustrates an assembled view of a holding portion and a detecting portion of the detachable boiling point detector for brake fluid.

Please refer to FIG. 6. The assembling end 35 of the detecting portion 31 is detachably fitted over the connecting portion 18 of the holding portion 11. In this embodiment, the first port 42 and the second port 22 are respectively a plug connector and a receptacle connector. Therefore, the first port 42 and the second port 22 are combined with each other at a connection between the assembling end 35 and the connecting portion 18 when the detecting portion 31 is connected to the holding portion 11. Accordingly, when the heater 43 or other electronic components in the detecting portion 31 is damaged, a user can just detach the detecting portion 31 from the connecting portion 18 and detach the first port 42 from the second port 22 for replacing a new detecting portion 31. Furthermore, when the detector is not in use or need to be packaged, the detecting portion 31 and the holding portion 11 can be detached from each other to reduce the volume and the occupied space of the detector.

Figure 7:
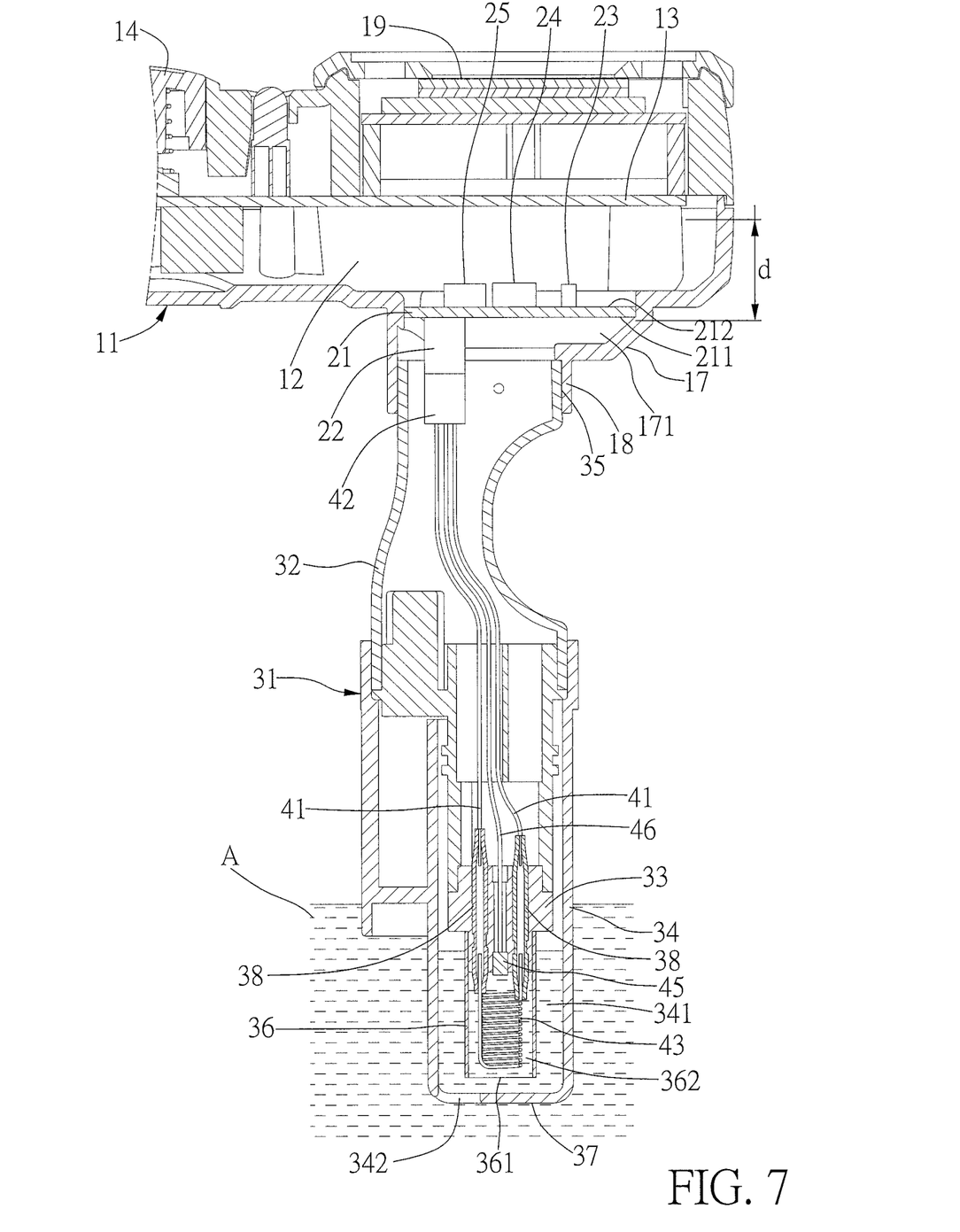
FIG. 7 illustrates an operational schematic view of the detachable boiling point detector for brake fluid.

Please refer to FIG. 7. In operation, the detecting portion 31 is immersed into a brake fluid A along a length direction of the detecting portion 31, so that the brake fluid A enters into the second heating space 341 through the first through hole 342 and the second through hole 343 of the cover 34, and then the brake fluid A further enters into the first heating space 36 through the opening 361 of the copper pipe 36. Next, the switch 14 is pressed to allow the heater 43 to heat up the brake fluid A in the first heating space 36, the first temperature sensor 45 detects a temperature of the brake fluid A heating to the boiling point and transmits the temperature to the second circuit board 21, and the second temperature sensor 23 on the second circuit board 21 detects a temperature on the second circuit board 21. Next, according to the difference between the temperature detected by the first temperature sensor 45 and the temperature detected by the second temperature sensor 23, the temperature compensation component 24 performs a temperature compensation process to remove the influence of the ambient temperature toward the brake fluid A. Then, the actual temperature of the brake fluid A is converted into a temperature signal, and the temperature signal is amplified by the temperature signal amplifier 25 and transmitted to the first circuit board 13, so that a detection result is displayed on the display 19.

In the embodiment, the second temperature sensor 23, the temperature compensation component 24, and the temperature signal amplifier 25 are assembled on the second circuit board 21 distant from the first circuit board 13 by the distance d. Therefore, the noises and the heat generated by the electronic components on the first circuit board 13 during the operation would not affect the temperature determination of the second temperature sensor 23, the temperature compensation component 24, and the temperature signal amplifier 25, thereby improving the accuracy of the measurement.

Furthermore, the second circuit board 21 is assembled in the chamber 171 of the holding portion 11 to block the receiving space 12 from communicating with the connecting portion 18. Therefore, when the vapor of the brake fluid generated by the boiling brake fluid in the sleeve member 32 flows upwardly and flows to the connecting portion 18, the vapor of the brake fluid is blocked by the second circuit board 21, so that the electronic components on the first circuit board 13 can be prevented from being damaged by the vapor of the brake fluid. In addition, since the second temperature sensor 23, the temperature compensation component 24, and the temperature signal amplifier 25 are assembled on the side surface 212 of the second circuit board 21 distant from the connecting portion 18. Therefore, the accuracy of the detection of the detector would not be affected by the vapor of the brake fluid.

What is claimed is:

1. A detachable boiling point detector for brake fluid comprising a holding portion and a detecting portion connected to the holding portion, a receiving space formed in the holding portion and a first circuit board assembled in the receiving space, the first circuit board having a switch being controllable out of the holding portion, a heater assembled to the detecting portion;

wherein the detecting portion comprises a sleeve member, a plug, and a cover, the two ends of the sleeve member are hollowed and tubular shaped, one of the two ends of the sleeve member forms an assembling end, the plug has a first extending portion and a second extending portion extending opposite to the first extending portion, an engaging block is protruding from the first extending portion, the first extending portion of the plug is assembled in the sleeve member, the engaging block of the plug is engaged with an engaging groove of the sleeve member, a copper pipe is fitted over the second extending portion of the plug, the copper pipe has an opening, a first heating space is formed in the copper pipe, the cover is hollowed and is fitted over the sleeve member to cover the plug and the copper pipe to form a detecting end; one side of the holding portion has a connecting portion, the assembling end is detachably connected to the connecting portion, the heater and a first temperature sensor are assembled on the detecting end, the heater and the first temperature sensor are connected to a first port located at the assembling end via a wire, respectively, a second circuit board is assembled in the receiving space of the holding portion and adjacent to the connecting portion, and the second circuit board is electrically connected to the first circuit board, a distance is between the second circuit board and the first circuit board, the second circuit board has a first side surface facing the connecting portion, and a second port is assembled on the first side surface of the second circuit board, the first port is detachably combined with the second port, and wherein when the detecting portion is connected to the holding portion, the first port and the second port are combined with each other at a connection between the assembling end and the connecting portion.

2. The detachable boiling point detector for brake fluid according to claim 1, wherein two ends of the connecting portion are hollowed, the holding portion has a head portion, and one side of the head portion has a protruding portion adjacent to the connecting portion, a chamber is formed in the protruding portion and in communication with the receiving space and the connecting portion, the second circuit board is assembled in the chamber to block the receiving space from communicating with the connecting portion.

3. The detachable boiling point detector for brake fluid according to claim 2, wherein the assembling end of the detecting portion is detachably fitted over the connecting portion and fastened by a locking member.

4. The detachable boiling point detector for brake fluid according to claim 1, wherein the second circuit board has a second side surface distant from the connecting portion, a second temperature sensor, a temperature compensation component, and a temperature signal amplifier are assembled on the second side surface of the second circuit board, wherein when a temperature detected by the first temperature sensor is transmitted to the second circuit board, the second temperature sensor on the second circuit board detects a temperature on the second circuit board, the temperature compensation component performs a temperature compensation process to obtain a compensated temperature according to a difference between the temperature detected by the first temperature sensor and the temperature detected by the second temperature sensor, the temperature signal amplifier amplifies a temperature signal of the compensated temperature and transmits the amplified signal to the first circuit board, and a detection result is displayed on a display.

5. The detachable boiling point detector for brake fluid according to claim 1, wherein a second heating space is formed between the cover and the copper pipe, a notch is recessed from the second extending portion of the plug and in communication with the first heating space and the second heating space.

6. The detachable boiling point detector for brake fluid according to claim 1, wherein two conductive tubes are passing through the plug, and the two conductive tubes are spaced from and aligned parallel with each other, one of two ends of each of the two conductive tubes is extending out of the first extending portion to form a first end toward the sleeve member, and the other end of each of the two conductive tubes is extending out of the second extending portion to form a second end distant from the sleeve member, the first ends of the two conductive tubes are connected to the first port at the assembling end via the wire of the heater, and two inserting ends of the heater are respectively inserted into and fastened with the second ends of the two conductive tubes.

7. The detachable boiling point detector for brake fluid according to claim 6, wherein a through hole is defined through an axial direction of the plug, the first temperature sensor is assembled in the through hole and in communication with the first heating space, the wire of the first temperature sensor passes through the through hole to be connected to the first port.

* * * * *